United States Patent
Beger et al.

(10) Patent No.: US 6,719,758 B2
(45) Date of Patent: Apr. 13, 2004

(54) KIRSCHNER WIRE WITH A HOLDING DEVICE FOR SURGICAL PROCEDURES

(75) Inventors: Jens Beger, Tuttlingen (DE); Rudolf Zepf, Wurmlingen (DE); Rudolf Beisse, Murnau (DE); Michael Potulski, Murnau (DE)

(73) Assignee: Aesculap AG & Co. KG, Tuttlingen (DE)

( * ) Notice: Subject to any disclaimer, the term of this patent is extended or adjusted under 35 U.S.C. 154(b) by 11 days.

(21) Appl. No.: 10/038,378

(22) Filed: Jan. 3, 2002

(65) Prior Publication Data

US 2002/0099309 A1 Jul. 25, 2002

Related U.S. Application Data

(60) Provisional application No. 60/262,968, filed on Jan. 19, 2001.

(51) Int. Cl.[7] ............................ A61B 17/84; A61B 17/56
(52) U.S. Cl. ............................ 606/60; 606/72; 606/104
(58) Field of Search .................... 606/62, 67, 72, 606/96, 97, 99, 100, 103, 104

(56) References Cited

U.S. PATENT DOCUMENTS

| 4,157,714 | A | * | 6/1979 | Foltz et al. | |
| 5,476,467 | A | * | 12/1995 | Benoist | 606/100 |
| 5,697,934 | A | * | 12/1997 | Huebner | 606/103 |
| 5,800,440 | A | * | 9/1998 | Stead | 606/104 |
| 6,015,413 | A | * | 1/2000 | Faccioli et al. | 606/104 |
| 6,019,762 | A | * | 2/2000 | Cole | 606/72 |
| 6,066,143 | A | * | 5/2000 | Lane | 606/104 |
| 6,264,661 | B1 | * | 7/2001 | Jerger et al. | 606/100 |
| 6,273,893 | B1 | * | 8/2001 | McAllen, III et al. | 606/104 |
| 6,309,396 | B1 | * | 10/2001 | Ritland | 606/96 |
| 6,402,759 | B1 | * | 6/2002 | Strong et al. | 606/104 |

FOREIGN PATENT DOCUMENTS

WO    WO 96/39975    12/1996

OTHER PUBLICATIONS

Catalogue pages showing Kirschner Wires, Aesculap AG & Co. KG, 1991 (2 pages).
*Colibri Instruction Manual*, Synthes, 1999 (7 pages).

* cited by examiner

Primary Examiner—Cary E. O'Connor
(74) Attorney, Agent, or Firm—Barry R. Lipsitz; Douglas M. McAllister

(57) ABSTRACT

A Kirschner wire 10 for use in endoscopic surgery is provided, as well as methods and apparatus for installing and removing Kirschner wire 10. Kirschner wire 10 has a holding device 20 for ease of insertion and removal. Kirschner wire 10 is sufficiently short so as not to protrude from the working channel of the endoscope. Insertion instrument 30 has a receptacle 40 which for engagement with holding device 20 of Kirschner wire 10. A targeting ring 46 on insertion instrument 30 enables placement of Kirschner wire 10 under x-ray supervision. Removal device 60 has a wire body 62 with a receptacle 64 located at a distal end thereof for engagement with holding device 20 of Kirschner wire 10. Kirschner wire 10 may be adapted for use in marking a point of entry for a cannulated bone screw or as a point of orientation for an endoscopic procedure.

49 Claims, 3 Drawing Sheets

KIRSCHNER WIRE WITH A HOLDING DEVICE FOR SURGICAL PROCEDURES

This application claims the benefit of U.S. provisional patent application No. 60/262,968 filed on Jan. 19, 2001.

BACKGROUND OF THE INVENTION

The present invention relates to a Kirschner wire for use in endoscopic surgery, as well as methods and apparatus for installing and removing the Kirschner wire. In particular, the present invention relates to a Kirschner wire having a holding device at a proximal end for ease of insertion and removal of the Kirschner wire. The Kirschner wire is sufficiently short so as not to protrude from the working channel of the endoscope. The insertion instrument has a receptacle which is adapted to engage with the holding device of the Kirschner wire. A targeting ring on the insertion instrument enables placement of the Kirschner wire under x-ray supervision. A removal device has a wire body with a receptacle located at a distal end thereof for engagement with the holding device of the Kirschner wire. The Kirschner wire may be adapted for use in marking a point of entry for a cannulated bone screw or as a point of orientation for an endoscopic procedure.

During endoscopic surgical procedures, such as spinal surgeries and the like, there is normally a single working channel provided by the endoscope. For surgical techniques that require the use of a Kirschner wire, the Kirschner wire may protrude from the working channel once in place. Alternatively, a shorter Kirschner wire may be used that does not protrude from the working channel. However, removal of such short Kirschner wires are difficult.

It would be advantageous to provide a sufficiently short Kirschner wire that does not protrude from the working channel of an endoscope, but that is easily removed. It would also be advantageous to provide a holding device on the proximal end of the Kirschner wire to aid in removal of the Kirschner wire. It would be further advantageous to provide an insertion instrument for placing such a short Kirschner wire endoscopically and a removal device for removing said short Kirschner wire endoscopically. It would be still further advantageous to provide a targeting ring to aid in the placement of the Kirschner wire under x-ray supervision.

The methods and apparatus of the present invention provide the foregoing and other advantages.

SUMMARY OF THE INVENTION

The present invention relates to a Kirschner wire for use in endoscopic surgery, as well as methods and apparatus for installing and removing the Kirschner wire. In particular, the present invention relates to a Kirschner wire having a holding device at a proximal end for ease of insertion and removal of the Kirschner wire. The Kirschner wire is sufficiently short so as not to protrude from the working channel of the endoscope. The insertion instrument has a receptacle which is adapted to engage with the holding device of the Kirschner wire. A targeting ring on the insertion instrument enables placement of the Kirschner wire under x-ray supervision. A removal device has a wire body with a receptacle located at a distal end thereof for engagement with the holding device of the Kirschner wire. The Kirschner wire may be adapted for use in marking a point of entry for a cannulated bone screw or as a point of orientation for an endoscopic procedure.

In an exemplary embodiment, a Kirschner wire for use in endoscopic procedures is provided. The Kirschner wire has a wire body with distal and proximal ends. A holding device is provided at the proximal end of the wire body for use in installing and removing the wire. The Kirschner wire may have a trocar point at the distal end of the wire body.

In a preferred embodiment, the holding device comprises external threads on the proximal end of the wire body. Those skilled in the art will appreciate that the holding device may also comprise internal threads on a cannulated portion of the proximal end of the wire body. The threads may be fine-pitch threads. Alternatively, the holding device may comprise any other type of interlocking mechanism which can be mated to a corresponding mechanism on an insertion instrument or a removal device for use in installing and removing the Kirschner wire during a surgical procedure.

Regardless of the nature of the holding device, it is preferable if the diameter of the holding device is equal to or less than a diameter of the wire body. This enables the wire to be removed through a cannulated instrument, such as a cannulated screwdriver.

It is preferable if the Kirschner wire is sufficiently short so as not to protrude from the working channel of an endoscope. In an exemplary embodiment of the invention, the length of the wire body is approximately 80 mm and the diameter of the wire body is approximately 2 mm.

The Kirschner wire may be adapted for use with an endoscope to provide a defined entry point for a bone screw or a defined point of orientation for an endoscopic procedure.

The Kirschner wire may be placed endoscopically using an insertion instrument. The insertion instrument has a hollow tube body for guiding the Kirschner wire. A plunger within the hollow tube body has a receptacle at a distal end thereof for engagement with the holding device of the Kirschner wire. A piston is connected to the plunger for use in driving the Kirschner wire to a desired depth (e.g., into a bone segment). A housing at the proximal end of the tube body is provided for guiding the piston. A metal targeting ring is provided on the housing for guiding the placement of the Kirschner wire using x-ray supervision.

The holding device may comprise external threads on the proximal end of the Kirschner wire. In such an embodiment, the receptacle will comprise corresponding internal threads on the distal end of the plunger. As discussed above, the holding device and the corresponding receptacle on the insertion instrument (and the removal device as discussed below) may take a variety of forms.

Where the holding device comprises threads, the Kirschner wire can be disengaged from the plunger by turning the plunger.

Preferably, the diameter of the holding device is equal to or less than a diameter of the Kirschner wire.

A stop may be provided at the distal end of the tube body for limiting a driving depth of the Kirschner wire.

In a further embodiment, a handle may be provided on the insertion instrument which extends transversely from the housing. The handle may be detachable.

The Kirschner wire may be removed endoscopically using removal device. The removal device has a wire body with a receptacle located at a distal end thereof for engagement with the holding device of the Kirschner wire. A handle is provided at a proximal end of the wire body for use in pulling the wire body after engagement with the Kirschner wire.

In one embodiment, the holding device comprises external threads on the proximal end of the Kirschner wire. In such an embodiment, the receptacle of the removal device comprises corresponding internal threads on the distal end of the wire body of the removal device. The diameter of the holding device is preferably equal to or less than the diameter of the Kirschner wire. In addition, the wire body of the removal device preferably has a diameter equal to a diameter of the Kirschner wire.

The removal device may be adapted for insertion into a cannulated insertion device. Alternatively, the removal device may be adapted for insertion into a cannulated screwdriver.

The invention also provides for a system for endoscopic insertion and removal of a Kirschner wire. The system consists of the insertion instrument, the removal device, and the Kirschner wire. The Kirschner wire has a first wire body with distal and proximal ends. A holding device is provided at the proximal end of the first wire body for use in installing and removing the Kirschner wire.

The insertion instrument for inserting the Kirschner wire has a hollow tube body for guiding the Kirschner wire. A plunger located within the hollow tube body has a first receptacle at a distal end thereof for engagement with the holding device of the Kirschner wire. A piston connected to the plunger is provided for use in driving the wire to a desired depth. A housing is provided at the proximal end of the tube body for guiding the piston. A metal targeting ring is provided on the housing for guiding the placement of the Kirschner wire using x-ray supervision.

A removal device for removing the Kirschner wire has a second wire body with a second receptacle located at a distal end thereof for engagement with the holding device of the Kirschner wire. A handle located at a proximal end of the wire body is provided for use in pulling the wire body after engagement with the Kirschner wire. In this manner, the Kirschner wire can be detached from the bone segment and removed from the endoscope.

The Kirschner wire further comprises a trocar point at the distal end of the first wire body.

The holding device may comprise external threads on the proximal end of the first wire body. The first receptacle may comprise corresponding internal threads on the distal end of the plunger. The second receptacle may also comprise corresponding internal threads on the distal end of the second wire body. The external and internal threads may be fine-pitch threads. In such an embodiment, the Kirschner wire car be disengaged from the plunger of the insertion instrument by turning the plunger.

The diameter of the holding device is equal to or less than a diameter of the first wire body of the Kirschner wire. The length of the Kirschner wire body is approximately 80 mm and the diameter of the Kirschner wire body is approximately 2 mm.

The Kirschner wire provides at least one of a defined entry point for a bone screw and a defined point of orientation for an endoscopic procedure.

A stop at the distal end of the tube body of the insertion instrument may be provided for limiting a driving depth of the wire. In addition, a handle may be provided on the insertion instrument extending transversely from the housing. The handle may be detachable.

In a preferred embodiment, the second wire body of the removal device has a diameter equal to a diameter of the first wire body of the Kirschner wire.

The removal device is adapted for insertion into a cannulated insertion device. Alternatively, the removal device is adapted for insertion into a cannulated screwdriver.

A method for inserting a Kirschner wire is also provided. A Kirschner wire having a holding device at a proximal end thereof is inserted into a distal cannulated end of a hollow tube body of an insertion instrument. The holding device of said Kirschner wire is engaged with a receptacle of a plunger within said hollow tube body. The Kirschner wire is positioned during a surgical procedure using an x-ray device. The Kirschner wire is driven into a bone segment by striking a piston connected to the plunger. Once driven into the bone segment in the appropriate position, the Kirschner wire may be disengaged from the plunger.

The holding device may comprise external threads on the proximal end of the wire body. The receptacle may comprise corresponding internal threads on the distal end of the plunger. In such an embodiment, the step of engaging the holding device with the receptacle comprises threading the Kirschner wire into the distal end of the plunger. The step of disengaging the Kirschner wire from the plunger comprises unthreading the plunger from the Kirschner wire.

A metal targeting ring may be provided on a housing of the insertion instrument to aid in positioning of the Kirschner wire using the x-ray device.

A method for removal of a Kirschner wire from a bone segment is provided. A cannulated instrument is inserted over the Kirschner wire. A removal instrument is introduced into the cannulated instrument. A receptacle located at a distal end of the removal instrument is engaged with a holding device located at the proximal end of the Kirschner wire. A handle at a proximal end of said removal instrument is pulled to disengage said Kirschner wire from the bone segment.

The cannulated instrument may comprise an insertion instrument. Alternatively, the cannulated instrument may be a cannulated screwdriver.

BRIEF DESCRIPTION OF THE DRAWINGS

The present invention will hereinafter be described in conjunction with the appended drawing figures, wherein like numerals denote like elements, and.

DETAILED DESCRIPTION OF THE INVENTION

The present invention relates to a Kirschner wire for use in endoscopic surgery, as well as methods and apparatus for installing and removing the Kirschner wire.

The ensuing detailed description provides exemplary embodiments only, and is not intended to limit the scope, applicability, or configuration of the invention. Rather, the ensuing detailed description of the exemplary embodiments will provide those skilled in the art with an enabling description for implementing a preferred embodiment of the invention. It should be understood that various changes may be made in the function and arrangement of elements without departing from the spirit and scope of the invention as set forth in the appended claims.

Figure 1:
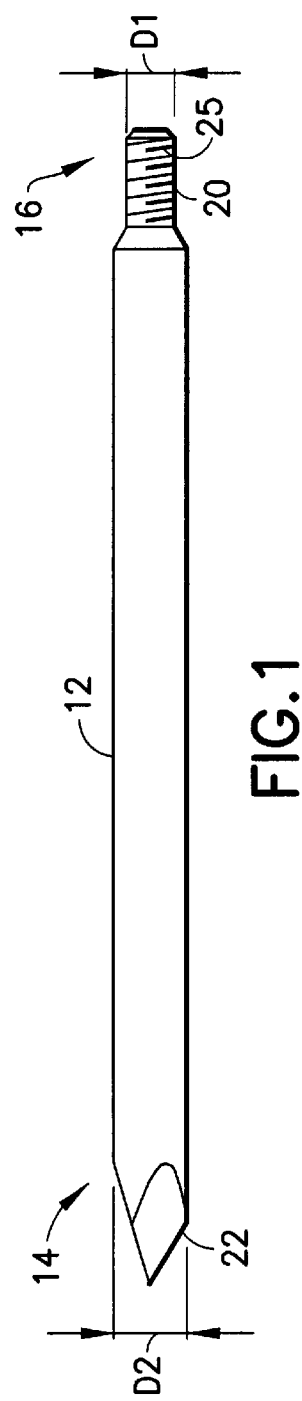
FIG. 1 shows an exemplary embodiment of a Kirschner wire in accordance with the invention.

In an exemplary embodiment as shown in FIG. 1, a Kirschner wire 10 for use in endoscopic procedures is provided. The Kirschner wire 10 has a wire body 12 with a distal end 14 and a proximal end 16. A holding device 20 is provided at the proximal end 16 of the wire body 12 for use in installing and removing the wire 10. The Kirschner wire 10 may have a trocar point 22 at the distal end 14 of the wire body 12.

As shown in FIG. 1, the holding device 20 may comprise external threads 25 on the proximal end 16 of the wire body 12. Those skilled in the art will appreciate that the holding device 20 may also comprise internal threads on a cannulated portion of the proximal end 16 of the wire body 10. The threads 25 may be fine-pitch threads. Alternatively, the holding device 20 may comprise any other type of interlocking mechanism, such as, e.g., bayonet type mounts, which can be mated to a corresponding mechanism on an insertion instrument or a removal device for use in installing and removing the Kirschner wire 10 during a surgical procedure.

Regardless of the nature of the holding device 20, it is preferable if its diameter D1 is equal to or less than a diameter D2 of the wire body 10. This enables the wire 10 to be removed through a cannulated instrument, such as a cannulated screwdriver.

It is preferable if the Kirschner wire 10 is sufficiently short so as not to protrude from the working channel of an endoscope. In an exemplary embodiment of the invention, the length of the wire body 12 is approximately 80 mm and the diameter of the wire body is approximately 2 mm.

The Kirschner wire 10 may be adapted for use with an endoscope to provide a defined entry point for a bone screw or a defined point of orientation for an endoscopic procedure.

Figure 2:
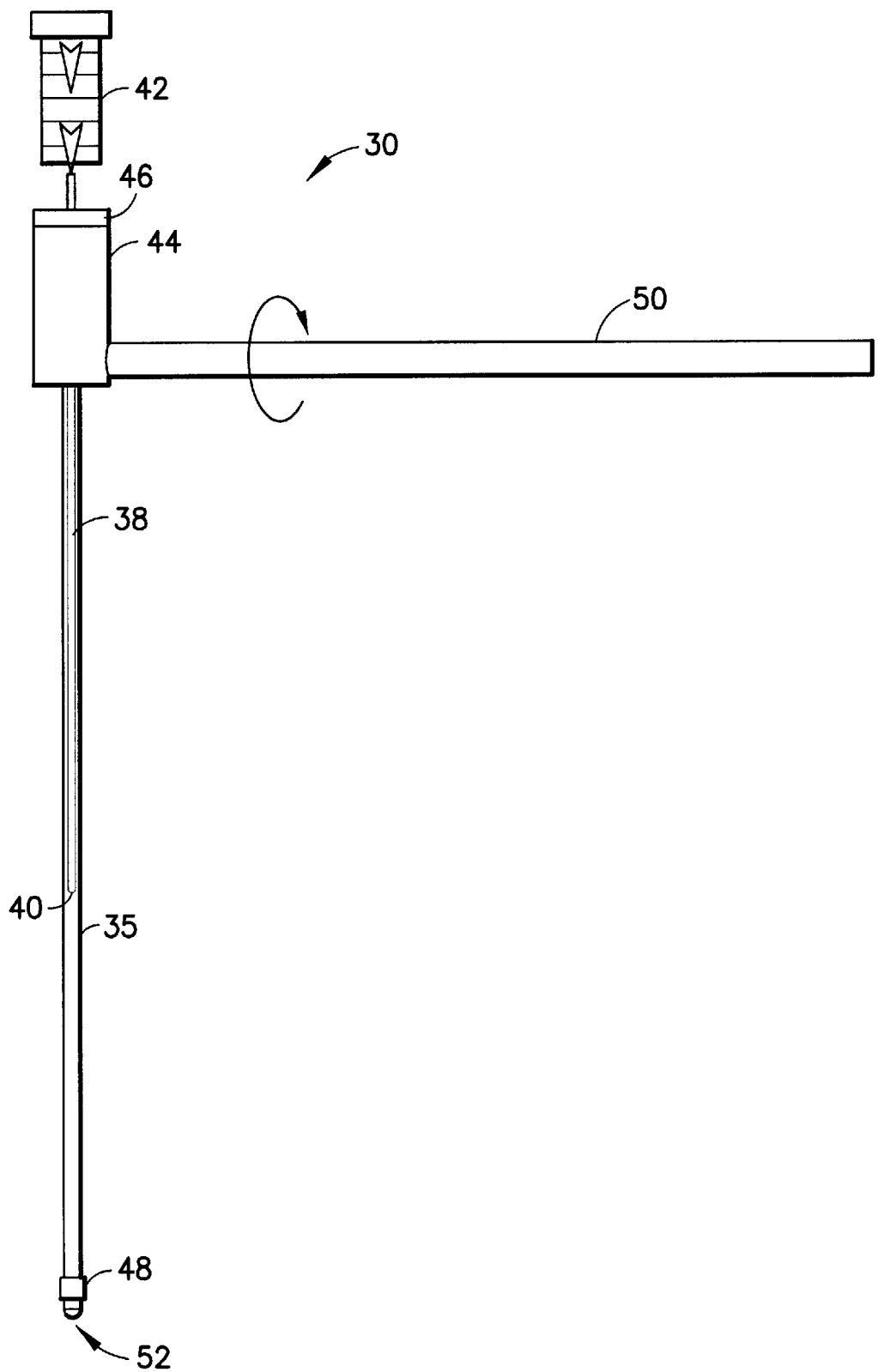
FIG. 2 shows an exemplary embodiment of an insertion instrument in accordance with the invention.

The Kirschner wire 10 may be placed endoscopically using an insertion instrument. As shown in FIG. 2, an example insertion instrument 30 has a hollow tube body 35 for guiding the Kirschner wire 10. The hollow tube body 35 is shown in FIG. 2 in a cutaway view for ease of explanation. A plunger 38 within the hollow tube body 35 has a receptacle 40 at a distal end thereof for engagement with the holding device 20 of the Kirschner wire 10. A piston 42 is connected to the plunger 38 for use in driving the Kirschner wire 10 to a desired depth (e.g., into a bone segment). A housing 44 at the proximal end of the tube body 35 is provided for guiding the piston 42. A metal targeting ring 46 is provided on the housing 44 for guiding the placement of the Kirschner wire 10 using x-ray supervision.

As discussed in connection with FIG. 1, the holding device 20 may comprise external threads 25 on the proximal end of the Kirschner wire 10. In such an embodiment, the receptacle 40 will comprise corresponding internal threads on the distal end of the plunger 38. As discussed above, the holding device 20 and the corresponding receptacle 40 on the insertion instrument (and on removal device as discussed below) may take a variety of forms. For example, the holding device 20 may alternatively comprise internal threads and the plunger 38 may comprise external threads. The details of one possible embodiment of a receptacle for use with the insertion instrument and the removal device are discussed below in connection with FIG. 5.

Where the holding device 20 comprises threads 25, the Kirschner wire 10 can be disengaged from the plunger 38 by turning the plunger 38.

A stop 48 may be provided at the distal end of the tube body 35 for limiting a driving depth of the Kirschner wire 10. The stop 48 can be adjustable, to allow the driving depth to be changed.

In a further embodiment, a handle 50 may be provided on the insertion instrument 30 which extends transversely from the housing 44. The handle 50 may be detachable.

Figure 3:
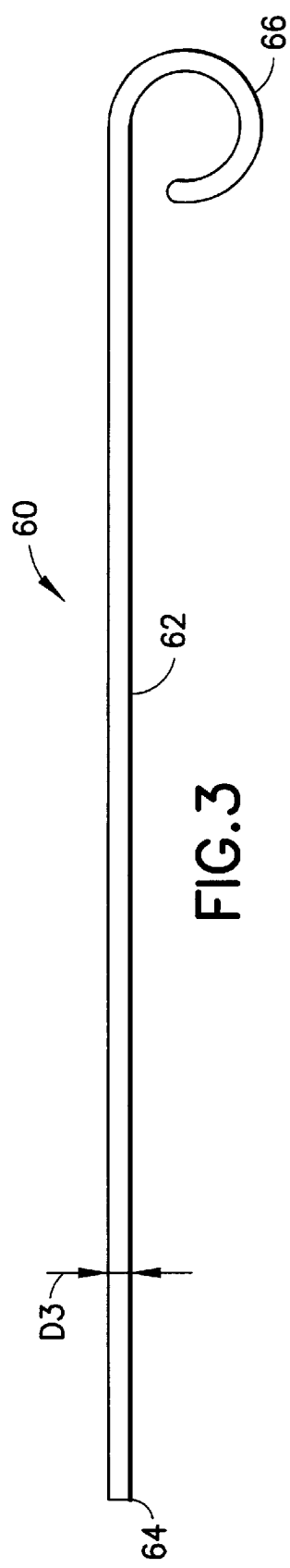
FIG. 3 shows an exemplary embodiment of a removal instrument in accordance with the invention.

The Kirschner wire 10 may be removed endoscopically using removal device. As shown in FIG. 3, one possible removal device 60 has a wire body 62 with a receptacle 64 located at a distal end thereof for engagement with the holding device 20 of the Kirschner wire 10. A handle 66 is provided at a proximal end of the wire body 62 for use in pulling the wire body 62 after engagement with the Kirschner wire 10. The handle 66 is shown in FIG. 3 as a curved portion of the wire body 62. Those skilled in the art will appreciate that the handle 66 may take a variety of forms.

As discussed in connection with FIG. 1, the holding device 20 of the Kirschner wire 10 may comprise external threads 25 on the proximal end of the Kirschner wire 10. In such an embodiment, the receptacle 64 of the removal device 60 will comprise corresponding internal threads on the distal end of the wire body 62 of the removal device 60. The wire body 62 of the removal device 60 preferably has a diameter D3 equal to a diameter of the Kirschner wire (D2 of FIG. 1). As mentioned above, the holding device 20 of the Kirschner wire may alternatively comprise internal threads, in which case the removal device 62 will comprise mating external threads.

The removal device 60 may be adapted for insertion into a cannulated insertion device. Alternatively, the removal device 60 may be adapted for insertion into a cannulated screwdriver.

The invention also provides for a system for endoscopic insertion and removal of a Kirschner wire 10. The system consists of the insertion instrument 30 described in connection with FIG. 2 or an equivalent, the removal device 60 described in connection with FIG. 3 or an equivalent, and the Kirschner wire 10 described in connection with FIG. 1 or an equivalent.

A method for inserting a Kirschner wire is also provided. A Kirschner wire (e.g., as shown in FIG. 1) having a holding device 20 at a proximal end thereof is inserted into a distal cannulated end 52 of a hollow tube body 35 of an insertion instrument (e.g., as shown in FIG. 2). The holding device 20 of the Kirschner wire 10 is engaged with a receptacle 40 of a plunger 38 within said hollow tube body 35. The Kirschner wire is positioned during a surgical procedure using an x-ray device (not shown) and is driven into a bone segment by striking the piston 42, which is connected to the plunger 38. Once driven into the bone segment in the appropriate position, the Kirschner wire 10 may be disengaged from the plunger 38.

The holding device 20 may comprise external threads 25 on the proximal end of the wire body 12 as shown in FIG. 1. The receptacle 40 may comprise corresponding internal threads on the distal end of the plunger 38. In such an embodiment, the step of engaging the holding device 20 with the receptacle 40 comprises threading the Kirschner wire 10 into the receptacle 40 at the distal end of the plunger 38. The step of disengaging the Kirschner wire 10 from the plunger comprises unthreading the plunger 38 from the Kirschner wire 10.

Figure 4A:
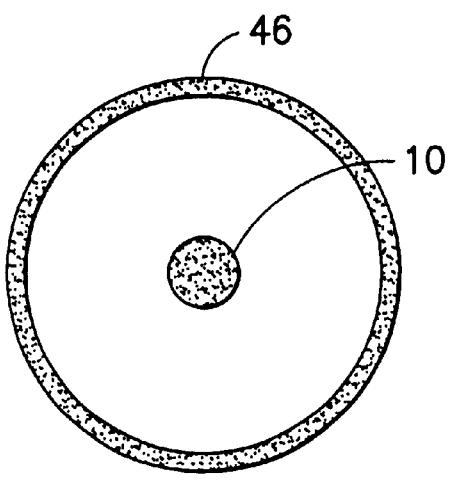
FIG. 4 shows the use of the targeting ring during insertion of the Kirschner wire.
Figure 4B:
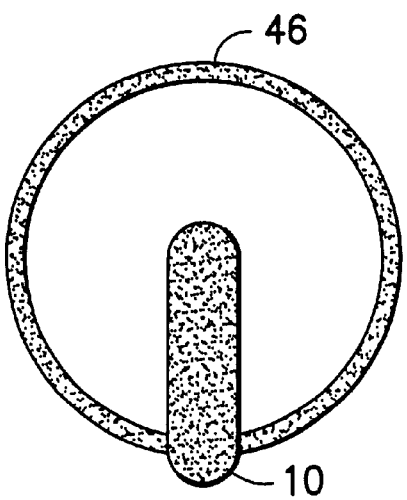

A metal targeting ring 46 may be provided on a housing 44 of the insertion instrument 30 to aid in positioning of the Kirschner wire 10 using the x-ray device. FIG. 4 shows the use of the targeting ring 46 during insertion of the Kirschner wire 10 during x-ray supervision. FIG. 4a shows a view of the position of the Kirschner wire 10 with respect to the targeting ring 46 when the Kirschner wire 10 is parallel to the path of the x-rays. FIG. 4b shows a view of the position of the Kirschner wire 10 with respect to the targeting ring 46 when the Kirschner wire 10 is not parallel to the path of the x-rays.

A method for removal of a Kirschner wire 10 from a bone segment is provided. A cannulated instrument is inserted over the Kirschner wire 10. A removal instrument 60 is introduced into the cannulated instrument. A receptacle 64 located at a distal end of the removal instrument 60 is engaged with a holding device 20 located at the proximal end of the Kirschner wire 10 (e.g., by threading the removal device 60 onto the holding device 20 of the Kirschner wire 10). A handle 66 at a proximal end of the removal instrument 60 is pulled to disengage said Kirschner wire 10 from the bone segment.

The cannulated instrument may comprise an insertion instrument. Alternatively, the cannulated instrument may be cannulated screwdriver. Cannulated instruments are well known in the art and the exact form of such an instrument is not critical to the use or function of the removal device 60.

Figure 5:
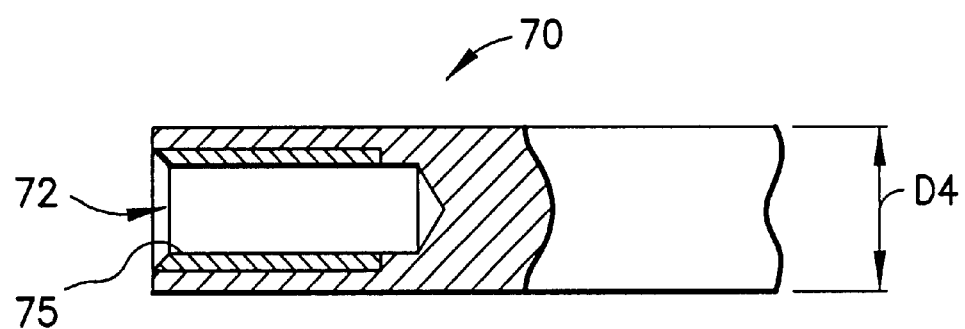
FIG. 5 shows an exemplary embodiment of a receptacle for use on an insertion instrument or a removal device.

FIG. 5 shows a receptacle 70 (e.g., receptacle 40 on the insertion instrument 30 of FIG. 2 and receptacle 64 of the removal device 60 of FIG. 3) for use with a Kirschner wire having a holding device 20 with external threads 25. The receptacle 70 is shown in a cutaway side view and has a cannulated end portion 72 adapted to receive the proximal end 16 of the Kirschner wire 10 of FIG. 1. The cannulated end portion 72 has internal threads 75 for engaging with the corresponding threads 25 of the holding device 20 of the Kirschner wire 10. The diameter D4 of the receptacle is preferably equal to the diameter D2 of the Kirschner wire 10.

Those skilled in the art will appreciate that the form of the receptacle 70 will coincide with the form of the holding device 20 of the Kirschner wire. In other words, the receptacle 70 will be adapted for engagement with the holding device 20 of the Kirschner wire 10. For example, where the holding device 20 comprises internal threads in a cannulated end of the Kirschner wire, the receptacle 70 will comprise corresponding external threads (e.g. on the plunger 38 of the insertion device 30 or on the wire body 62 of the removal device 60).

It should now be appreciated that the present invention provides an advantageous Kirschner wire, as well as advantageous methods and apparatus for installing and removing the Kirschner wire.

Although the invention has been described in connection with various illustrated embodiments, numerous modifications and adaptations may be made thereto without departing from the spirit and scope of the invention as set forth in the claims.

What is claimed is:

1. A Kirschner wire for use in endoscopic procedures, comprising:
   a wire body having distal and proximal ends; and
   a holding device at the proximal end of the wire body adapted for engagement with a device for installing and removing the wire, said holding device comprising external threads on the proximal end of the wire body;
   wherein a diameter of the holding device is no greater than a diameter of the wire body.

2. A Kirschner wire in accordance with claim 1, further comprising:
   a trocar point at the distal end of the wire body.

3. A Kirschner wire in accordance with claim 1, wherein: the threads are fine-pitch threads.

4. A Kirschner wire in accordance with claim 1, wherein: the length of the wire body is approximately 80 mm; and the diameter of the wire body is approximately 2 mm.

5. A Kirschner wire in accordance with claim 1, wherein: the wire is adapted for use with an endoscope to provide at least one of a defined entry point for a bone screw and a defined point of orientation for an endoscopic procedure.

6. A Kirschner wire in accordance with claim 5, wherein: the wire is adapted to be placed endoscopically using an insertion instrument.

7. An insertion instrument for endoscopic placement of a Kirschner wire having a holding device at a proximal end thereof, said insertion instrument comprising:
   a hollow tube body for guiding the Kirschner wire;
   a plunger within the hollow tube body having a receptacle at a distal end thereof for engagement with the holding device of the Kirschner wire;
   a piston connected to the plunger for use in driving the Kirschner wire to a desired depth;
   a housing at the proximal end of the tube body for guiding the piston; and
   a metal targeting ring on the housing for guiding the placement of the Kirschner wire using x-ray supervision.

8. An insertion instrument in accordance with claim 7, wherein said Kirschner wire has a trocar point at a distal end thereof.

9. An insertion instrument in accordance with claim 7, wherein:
   said holding device comprises external threads on the proximal end of the Kirschner wire; and
   said receptacle comprises internal threads on the distal end of the plunger.

10. An insertion instrument in accordance with claim 9, wherein:
    the Kirschner wire can be disengaged from the plunger by turning the plunger.

11. An insertion instrument in accordance with claim 7, wherein a diameter of the holding device is no greater than a diameter of the Kirschner wire.

12. An insertion instrument in accordance with claim 7, further comprising:
    a stop at the distal end of the tube body for limiting a driving depth of the wire.

13. An insertion instrument in accordance with claim 7, further comprising:
    a handle extending transversely from the housing.

14. An insertion instrument in accordance with claim 13, wherein said handle is detachable.

15. A removal device for removing a Kirschner wire from a bone segment, said Kirschner wire having a holding device at a proximal end thereof, said removal device comprising:
    a wire body having a receptacle located at a distal end thereof for engagement with the holding device of the Kirschner wire; and
    a handle at a proximal end of the wire body for use in pulling the wire body after engagement with the Kirschner wire, wherein:
    said holding device comprises external threads on the proximal end of the Kirschner wire; and
    said receptacle comprises internal threads on the distal end of the wire body of the removal device.

16. A removal device in accordance with claim 15, wherein said Kirschner wire has a trocar point at a distal end thereof.

17. A removal device in accordance with claim 15, wherein a diameter of the holding device is no greater than a diameter of the Kirschner wire.

18. A removal device in accordance with claim 15, wherein the wire body of the removal device has a diameter equal to a diameter of the Kirschner wire.

19. A removal device in accordance with claim 15, wherein said removal device is adapted for insertion into a cannulated insertion device.

20. A removal device in accordance with claim 15, wherein said removal device is adapted for insertion into a cannulated screwdriver.

21. A system for endoscopic insertion and removal of a Kirschner wire, comprising:

a Kirschner wire having:
 a first wire body with distal and proximal ends; and
 a holding device at the proximal end of the first wire body for use in installing and removing the Kirschner wire;

an insertion instrument for inserting the Kirschner wire, having:
 a hollow tube body for guiding the Kirschner wire;
 a plunger within the hollow tube body having a first receptacle at a distal end thereof for engagement with the holding device of the Kirschner wire;
 a piston connected to the plunger for use in driving the wire to a desired depth;
 a housing at the proximal end of the tube body for guiding the piston; and
 a metal targeting ring on the housing for guiding the placement of the Kirschner wire using x-ray supervision; and a removal device for removing the Kirschner wire, having:
 a second wire body having a second receptacle located at a distal end thereof for engagement with the holding device of the Kirschner wire; and
 a handle at a proximal end of the wire body for use in pulling the wire body after engagement with the Kirschner wire.

22. A system in accordance with claim 21, wherein said Kirschner wire further comprises a trocar point at the distal end of the first wire body.

23. A system in accordance with claim 21, wherein:
said holding device comprises external threads on the proximal end of the first wire body;
said first receptacle comprises internal threads on the distal end of the plunger; and
said second receptacle comprises internal threads on the distal end of the second wire body.

24. A system in accordance with claim 23, wherein:
the external and internal threads are fine-pitch threads.

25. A system in accordance with claim 23, wherein:
the Kirschner wire can be disengaged from the plunger by turning the plunger.

26. A system in accordance with claim 21, wherein a diameter of the holding device is no greater than a diameter of the first wire body of the Kirschner wire.

27. A system in accordance with claim 21, wherein:
the length of the Kirschner wire body is approximately 80 mm; and
the diameter of the Kirschner wire body is approximately 2 mm.

28. A system in accordance with claim 21, wherein:
the Kirschner wire provides at least one of a defined entry point for a bone screw and a defined point of orientation of an endoscopic procedure.

29. A system in accordance with claim 21, wherein the insertion instrument further comprises:
a stop at the distal end of the tube body for limiting a driving depth of the wire.

30. A system in accordance with claim 21, wherein the insertion instrument further comprises:
a handle extending transversely from the housing.

31. A system in accordance with claim 30, wherein said handle is detachable.

32. A system in accordance with claim 21, wherein the second wire body of the removal device has a diameter equal to a diameter of the first wire body of the Kirschner wire.

33. A system in accordance with claim 21, wherein:
said removal device is adapted for insertion into a cannulated insertion device.

34. A system in accordance with claim 21, wherein:
said removal device is adapted for insertion into a cannulated screwdriver.

35. A method for inserting a Kirschner wire, comprising the steps of:

inserting a Kirschner wire having a holding device at a proximal end thereof into a distal cannulated end of a hollow tube body of an insertion instrument;

engaging said holding device of said Kirschner wire with a receptacle of a plunger within said hollow tube body;

positioning the Kirschner wire during a surgical procedure using an x-ray device;

driving the Kirschner wire into a bone segment by striking a piston connected to the plunger; and disengaging the Kirschner wire from the plunger.

36. A method in accordance with claim 35, wherein:
said holding device comprises external threads on the proximal end of the wire body;
said receptacle comprises internal threads on the distal end of the plunger;
the step of engaging the holding device with the receptacle comprises threading the Kirschner wire into the distal end of the plunger; and
the step of disengaging the Kirschner wire from the plunger comprises unthreading the plunger from the Kirschner wire.

37. A method in accordance with claim 35, wherein a diameter of the holding device is no greater than a diameter of the Kirschner wire.

38. A method in accordance with claim 35, wherein a metal targeting ring is provided on a housing of the insertion instrument to aid in positioning of the Kirschner wire using the x-ray device.

39. A method in accordance with claim 35, wherein:
the length of the Kirschner wire body is approximately 80 mm; and
the diameter of the Kirschner wire body is approximately 2 mm.

40. A method in accordance with claim 35, wherein a stop is provided at the distal end of the tube body for limiting a driving depth of the Kirschner wire.

41. A method in accordance with claim 35, wherein a handle extends transversely from a housing of the insertion instrument.

42. A method in accordance with claim 41, wherein said handle is detachable.

43. A method in accordance with claim 35, wherein said Kirschner wire has a trocar point at a distal end thereof.

44. A method for removal of a Kirschner wire from a bone segment, comprising the steps of:
  inserting a cannulated instrument over said Kirschner wire;
  introducing a removal instrument into said cannulated instrument;
  engaging a receptacle located at a distal end of said removal instrument with a holding device located at the proximal end of said Kirschner wire; and
  pulling on a handle at a proximal end of said removal instrument to disengage said Kirschner wire from said bone segment.

45. A method in accordance with claim 44, wherein:
  said holding device comprises external threads on the proximal end of the Kirschner wire; and
  said receptacle comprises internal threads on the distal end of the removal device.

46. A method in accordance with claim 44, wherein a diameter of the holding device is no greater than a diameter of the Kirschner wire.

47. A method in accordance with claim 44, wherein said cannulated instrument comprises an insertion instrument.

48. A method in accordance with claim 44, wherein said cannulated instrument is a cannulated screwdriver.

49. A method in accordance with claim 44, wherein the removal device has a diameter equal to a diameter of the Kirschner wire.

* * * * *